US011628083B1

(12) United States Patent
Brown

(10) Patent No.: US 11,628,083 B1
(45) Date of Patent: Apr. 18, 2023

(54) NASAL DILATOR WITH COLUMELLA RETAINER FOR RESISTING WITHDRAWAL AND ADJUSTABLE SECTIONS FOR OPTIMIZING FIT, COMFORT, AND BREATHING PERFORMANCE

(71) Applicant: Gregory A. M. Brown, Reno, NC (US)

(72) Inventor: Gregory A. M. Brown, Reno, NC (US)

(73) Assignee: INTERNATIONAL PATENT DEVELOPMENT GROUP, LLC, Reno, NV (US)

( * ) Notice: Subject to any disclaimer, the term of this patent is extended or adjusted under 35 U.S.C. 154(b) by 334 days.

(21) Appl. No.: 16/830,173

(22) Filed: Mar. 25, 2020

(51) Int. Cl.
*A61F 5/08* (2006.01)

(52) U.S. Cl.
CPC .................................... *A61F 5/08* (2013.01)

(58) Field of Classification Search
CPC . A61F 5/08; A61F 5/56; A61M 15/08; A61M 15/085
USPC .......................................................... 606/199
See application file for complete search history.

(56) References Cited

U.S. PATENT DOCUMENTS

| | | | | |
|---|---|---|---|---|
| 5,727,543 | A | 3/1998 | Corsaro | |
| 5,831,852 | A | 11/1998 | Cahill-O'Brien et al. | |
| 5,850,834 | A | 12/1998 | Yoshida et al. | |
| 7,055,523 | B1 | 6/2006 | Brown | |
| 2003/0181941 | A1 | 9/2003 | Bruggisser et al. | |
| 2015/0000675 | A1* | 1/2015 | Kallikounis .............. | A61F 5/08 606/199 |
| 2015/0196420 | A1* | 7/2015 | Ede .......................... | A61F 5/08 604/285 |

* cited by examiner

*Primary Examiner* — Majid Jamialahmadi
(74) *Attorney, Agent, or Firm* — Norton Rose Fulbright US LLP

(57) ABSTRACT

An internal nasal dilator approximates a U-shape having a bight section and two elongated members with end pads. Each member can be custom formed for comfortable and secure placement in the respective nostrils. Insertion is limited when the bight section of the U contacts the bottom of the user's columella. The upper ends of the members transition to widened areas or pads that face outwardly and are shaped and sized to urge the outer wall of their respective nostril outwardly to dilate the nostril to facilitate breathing. The lower portions of the members have inwardly directed projections at a predetermined distance from the bight; these projections overlie the upper ledge of the columella to interfere with or block withdrawal of the dilator unless a sufficient downward force is exerted to enable the projections to slide off and past the ledge of the columella to allow the dilator to be withdrawn.

16 Claims, 6 Drawing Sheets

NASAL DILATOR WITH COLUMELLA RETAINER FOR RESISTING WITHDRAWAL AND ADJUSTABLE SECTIONS FOR OPTIMIZING FIT, COMFORT, AND BREATHING PERFORMANCE

BACKGROUND—CROSS-REFERENCE TO RELATED APPLICATION

This patent relates to an improved mechanical nasal dilator, especially to the dilator of U.S. Pat. No. 8,834,512, 2014 Sep. 16, to Gregory A. M. Brown et al.

1. Field

The field is breathing aids, in particular intranasal instruments for dilating human nasal passages.

2. Prior Art—Nasal Dilators

The Brown et al. '512 patent, supra, contains a list of prior-art nasal dilators and their characteristics and disadvantages, and is incorporated herein by reference. The purpose of nasal dilators, including those of the Brown et al. patent, supra, is to mechanically dilate a user's nasal passages to open the nasal airways to reduce snoring and obstructive sleep apnea (temporary cessations of breathing), reduce congestion, reduce mouth breathing and dry mouth, improve restful sleep, reduce stress, improve oxygen flow into the lungs and improve expelling carbon dioxide, improve athletic performance, and improve mental clarity, etc. Such dilators generally apply external or internal forces to urge a portion of one or both of the outer walls of the nostrils to move in a direction away from the nasal septum (the internal wall that divides the two nostrils), thereby enlarging or dilating the nostrils and permitting freer flow of air through the nose. Such dilating enables a user to breathe more freely through the nose, thereby reducing snoring, sleep apnea, and xerostomia (dry mouth condition) and improving other conditions such as restful sleep, improved oxygen flow, improved mental clarity and other performance enhancements.

The following additional patents relate to nasal dilators that grip the septum for retention in the nose.

L. Corsaro, in U.S. Pat. No. 5,727,543, 1998 Mar. 7, shows a U-shaped, bent wire nasal dilator where the legs of the U are looped. The outer portions of the loops urge the outer walls of the nostrils in a direction away from the septum. The inner portions of the loops rest against and squeeze the septum to prevent unwanted ejection of the dilator.

H. G. Brennan, in U.S. Pat. No. 5,931,852, 199 Aug. 3, shows a nasal comprises an elastomeric ribbon having a U-shaped or bight portion with legs that bend in toward each other and then extend away from the bight in two parallel legs. At the end of each leg an arm extends out perpendicularly. The two arms are initially parallel but then curve around to form two additional skewed U-shaped or semi-circular sections at the respective ends of each leg. The U-shaped arms are inserted into the respective nostrils so that they urge the nasal walls outward. The bight connecting the two legs fits around the bottom of the septum or columella and the parallel legs sandwich and grasp the septum to resist withdrawal.

T. W. Brown, in U.S. Pat. No. 7,055,523, 2006 Jun. 6, shows a dilator comprising a U-shaped portion with outwardly extending arms at the upper ends of the legs of the U. The arms terminate in pads that face outward. When the arms are inserted into the respective nostrils, the pads press against the outer walls of the nostrils, forcing them outward. The bight of the U at the bottoms of the legs fits around the bottom of the septum or columella and thickened portions of the upper ends of the legs sandwich and squeeze the septum to resist unwanted ejection of the device. This dilator also optionally stores and delivers chemical compounds.

I have found that most users of the above types of dilators fail to continue to use them after a short period because the devices create discomfort and pain in the nose, specifically the septum, due to pressure from the portions of the devices that sandwich and squeeze the septum. While such devices may dilate the nostrils and their squeezing or grasping of the septum enables the dilators to resist withdrawal, I have found that these advantages have not been of value because of the failure of users to continue to use the dilator. I.e., I have found that most users will not continue to use a dilator that is not comfortable and pain-free in use.

SUMMARY

In accordance with one preferred embodiment of one aspect, a human nasal dilator comprises a roughly U-shaped device having two legs that that the user inserts into the two nostrils, respectively. The extent of insertion is limited by the bight section of the U contacting the lower side or bottom of the user's septum, specifically the columella. The upper ends of the legs of the U have widened areas or pads that face outwardly and are shaped and sized to urge the outer wall of their respective nostril outwardly in order to dilate the nostril to facilitate breathing. The lower portions of the legs of the U have inwardly directed projections at a predetermined distance up from the bight portion; these projections overlie the upper ledge of the columella so that it will interfere with or block withdrawal of the dilator unless a sufficient downward force is exerted to enable the projections to slide off and past the ledge of the columella to allow the dilator to be withdrawn.

The bottom or bight section extends has on each end vertical sections (legs) that turn upwardly and these transition at the upper portion of the vertical sections into curved, upwardly and outwardly moving arms which turn vertically and transition into large generally flatter pads above each arm which is positioned generally parallel and outward of the vertical sections below and which apply outward force to outer walls of the nose. The sections of the dilator can be adjusted in many ways to improve retention, fit, comfort, breathing performance, and airflow volume.

Accordingly, some advantages of various aspects of our device are to provide an inexpensive, disposable, and adjustable dilator that is rugged, not bulky, installable by a lay user, unobtrusive, comfortable, and pain-free when worn, and does not require monitoring during use. Also, it is not easily dislodged and thus will remain more stably in place during use. Other advantages will become apparent from a review of these and other aspects and embodiments described below.

Figure 1:
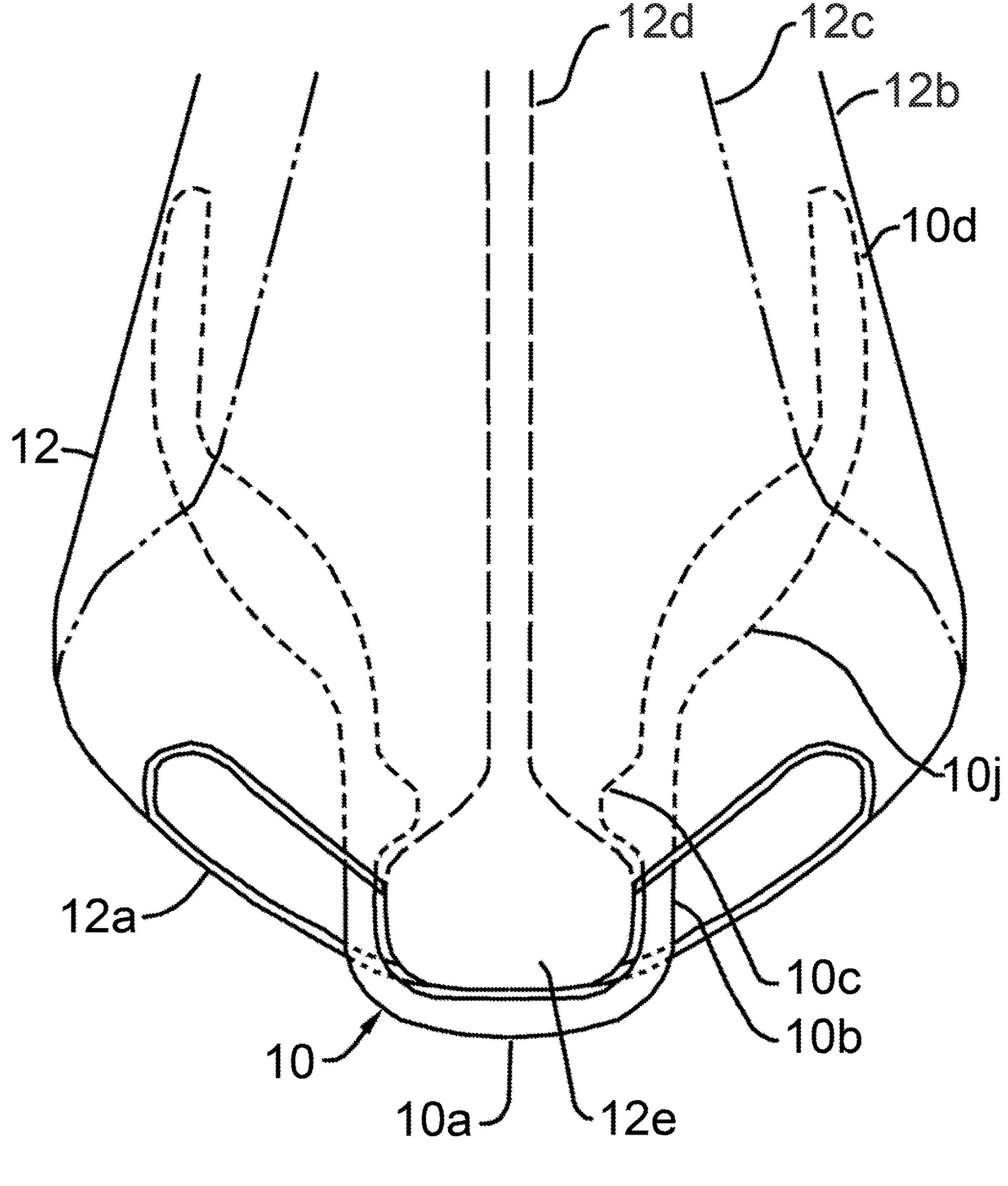
FIG. 1 is an elevational view, partly in phantom, of a substantially generic dilator installed in a user's nose and secured by retaining projections that overlie the user's columella.
Figure 2A:
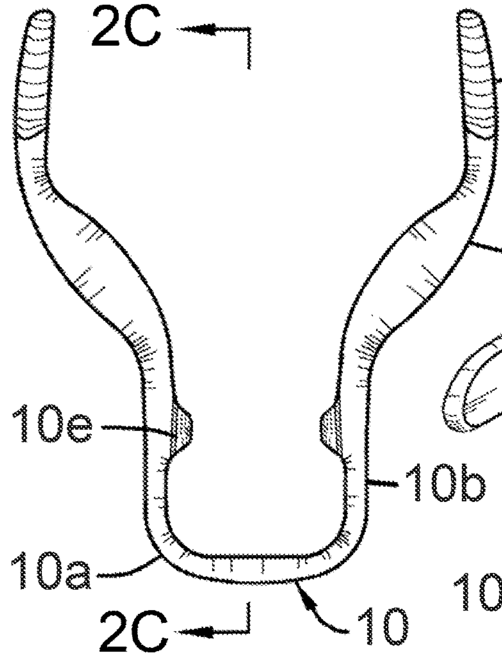
FIG. 2A is a front or elevational view of a dilator like FIG. 1.
Figure 2B:
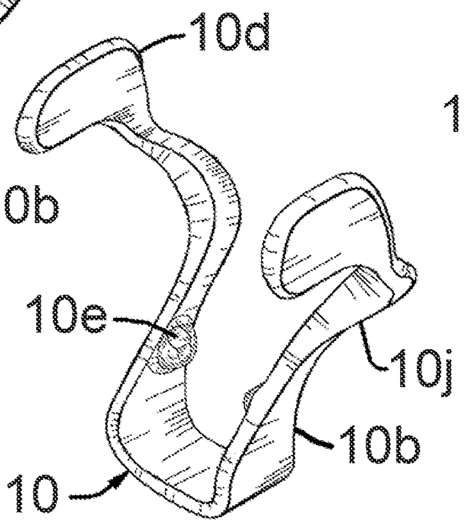
FIG. 2B is a perspective view from above of a dilator like FIG. 1.
Figure 2C:
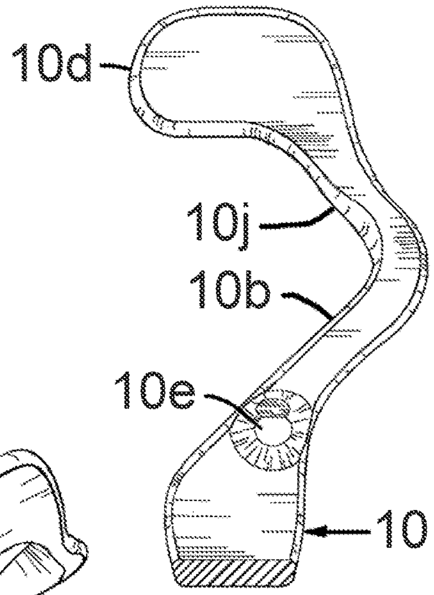
FIG. 2C is a partially sectional side view of a dilator like FIG. 1, The dilator of FIGS. 2A, 2B, and 2C is generally semispherical.
Figure 3A:
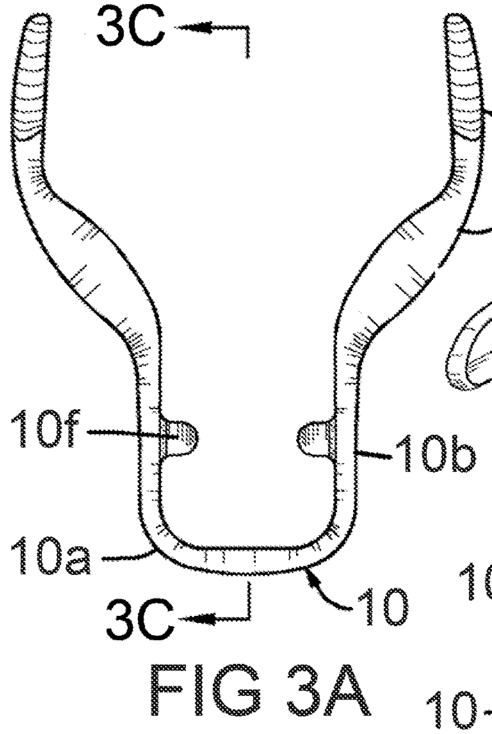
FIG. 3A is a front or elevational view of a dilator like FIG. 1.
Figure 3B:
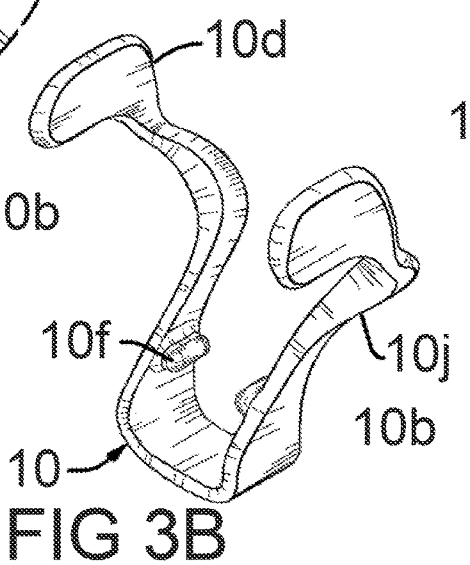
FIG. 3B is a perspective view from above of a dilator like FIG. 1.
Figure 3C:
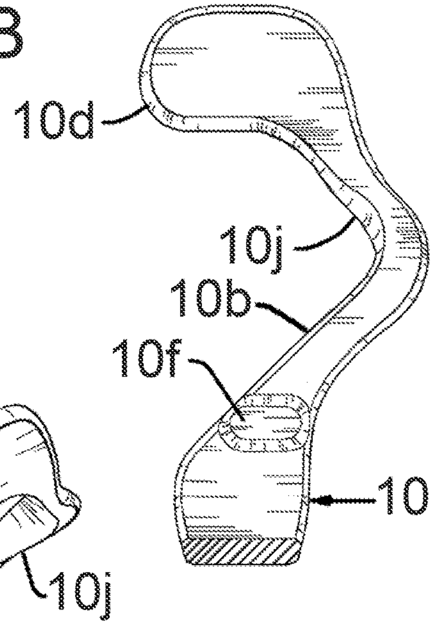
FIG. 3C is a partially sectional side view of a dilator like FIG. 1. The dilator of FIGS. 3A, 3B, and 3C is elongated with radius fillets and a rounded top and ends.
Figure 4A:
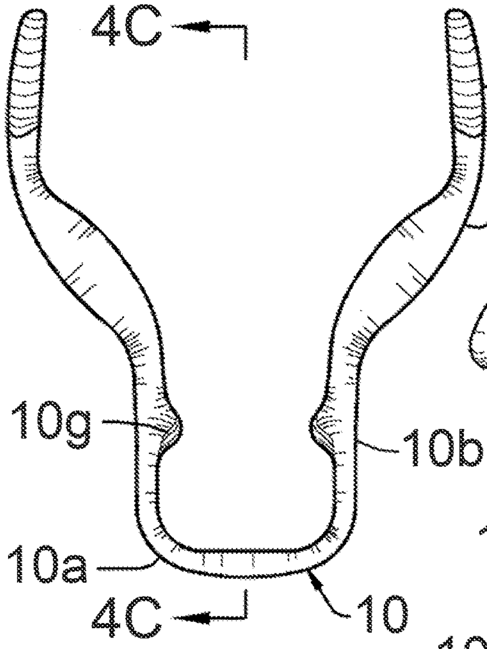
FIG. 4A is a front or elevational view of a dilator like FIG. 1.
Figure 4B:
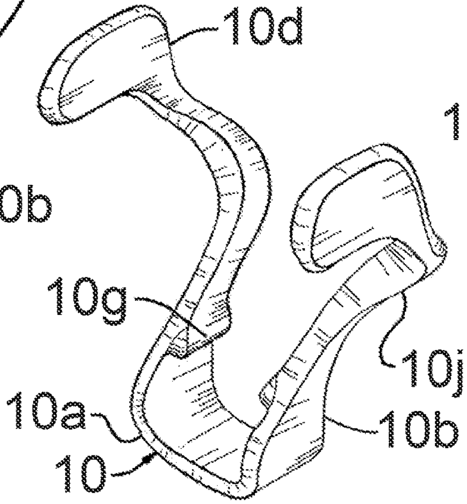
FIG. 4B is a perspective view from above of a dilator like FIG. 1.
Figure 4C:
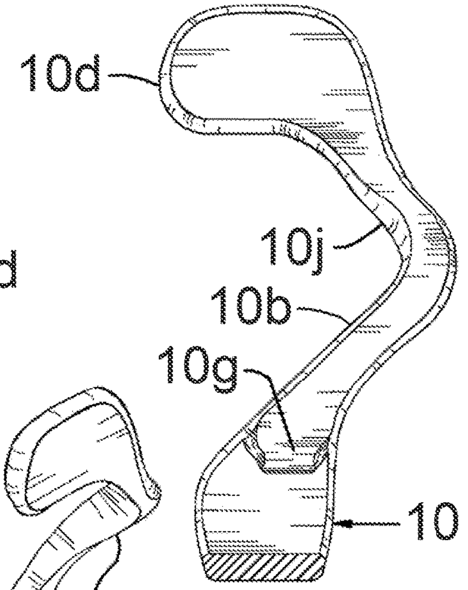
FIG. 4C is a partially sectional side view of a dilator like FIG. 1. The dilator of FIGS. 4A, 4B, and 4C is elongated with radiused forms including the ends and sloping slides.
Figure 5A:
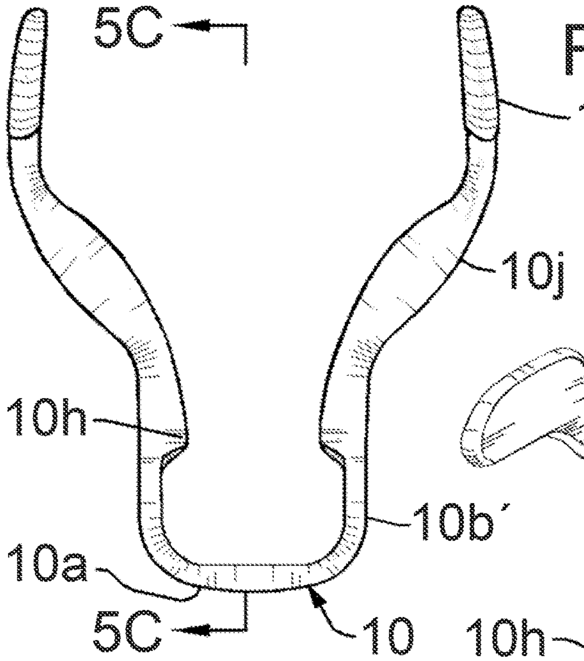
FIG. 5A is a front or elevational view of a dilator like FIG. 1.
Figure 5B:
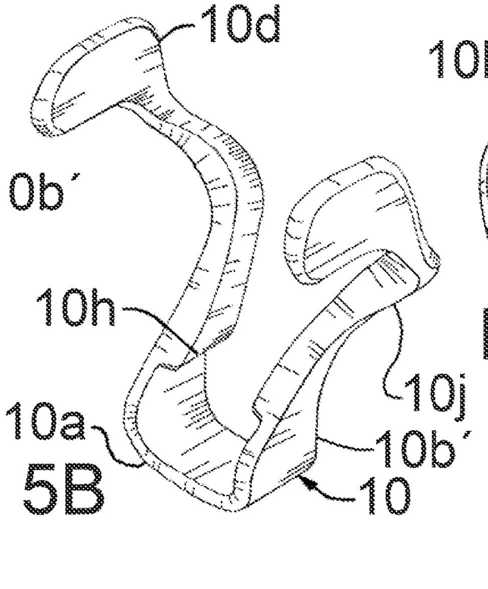
FIG. 5B is a perspective view from above of a dilator like FIG. 1.
Figure 5C:
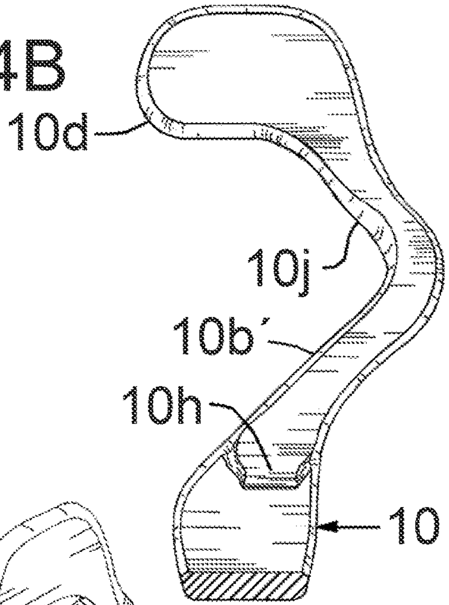
FIG. 5C is a partially sectional side view of a dilator like FIG. 1. The dilator of FIGS. 5A, 5B, and 5C has a cam shaped leg with an upwardly tapering undercut of the retention shelf.
Figure 6A:
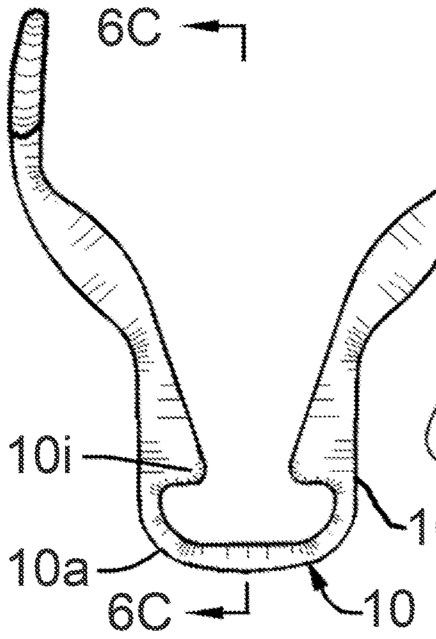
FIG. 6A is a front or elevational view of a dilator like FIG. 1.
Figure 6B:
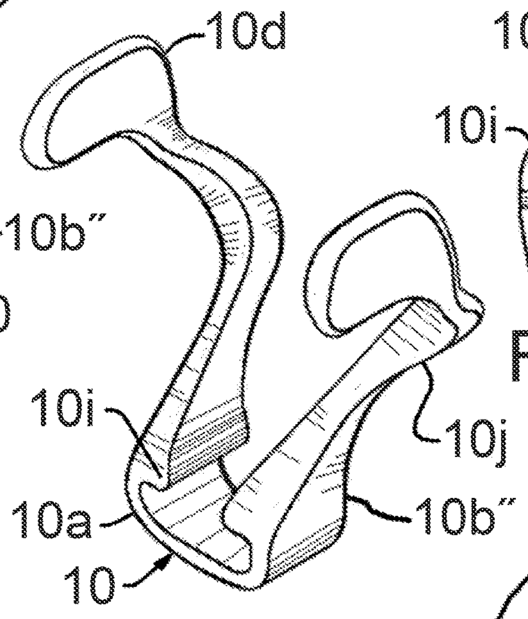
FIG. 6B is a perspective view from above of a dilator like FIG. 1.
Figure 6C:
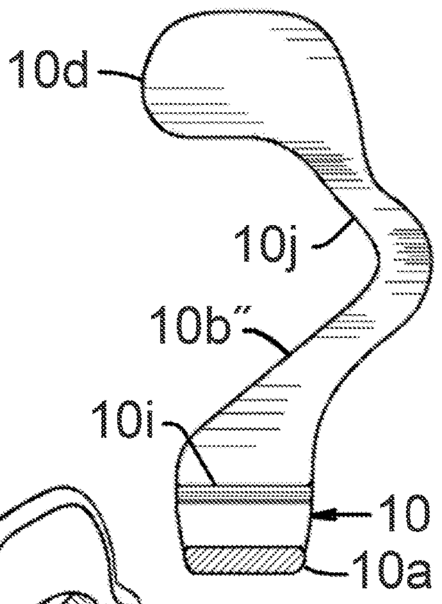
FIG. 6C is a partially sectional side view of a dilator like FIG. 1. The dilator of FIG. 6 has a sloping or ramping leg and a horizontal undercut of the retention shelf.

| DRAWING REFERENCE NUMERALS | |
|---|---|
| 10 | dilator |
| 10a | bight portion |
| 10b | leg/vertical section |
| 10c | protrusion of FIG. 1 |
| 10d | tip portion/pad |
| 10e | protrusion of FIGS. 2 |
| 10f | protrusion of FIGS. 3 |
| 10g | protrusion of FIGS. 4 |
| 10h | protrusion of FIGS. 5 |
| 10i | protrusion of FIGS. 6 |
| 10j | arm |
| 10k | notch |
| 10m | rotated tip portion |
| 10n | side tilted tip portion |
| 10o | original tip portion position |
| 10p | front tilted tip portion |
| 10q | arm (10j) in wider position |
| 10r | original position of leg/vertical section |
| 10s | leg widened |
| 12 | nose |
| 12a | nostril |
| 12b | nose side, dilated |
| 12c | nose side, undilated |
| 12d | septum |
| 12e | columella |
| 12f | parallel nostrils |
| 12g | angled nostrils |
| 12h | nasal airway |

DETAILED DESCRIPTION—FIG. 1—GENERAL EMBODIMENT

A dilator 10 is installed in a user's nose 12. Its visible portions where exposed in nostrils **12*a* at the bottom of the user's nose are shown in solid lines. Its portions inside the nose and shown in hidden (dashed) lines. The dilator comprises a generally U-shaped flat or ribbon member having a bottom base portion or bight portion 10*a*** and two elongated members or sides of the "U", which extend up from the base portion.

The lower portion of each member is a leg 10*b* and the upper portion of each member is an arm 10*j*. Each leg or lower portion is relatively close and parallel to that of the opposite leg and extends up generally perpendicularly to bight portion 10*a*. Further, each leg's lower portion has an inwardly extending protrusion 10*c*.

The arm or upper portion of each member has a widened middle portion that slopes outwardly and backwardly and then extends up vertically to free end with a tip portion 10*d*. Tip portion 10*d* presses or urges the user's nostril sides outwardly as shown by solid lines 12*b*. Top portion 10*d* is widened to provide a comfortable pad portion, as shown in FIGS. 2 to 6 and as explained in the above Brown '512 patent.

Lines 12*b* indicate the dilated or expanded sides of the nostrils. When the dilator is removed from the user's nose, the user's nostrils return to a normal, undilated position indicated by phantom (dash-dot-dot) lines 12*c*. The user's nose includes a septum 12*d* which has generally parallel sides, except for its bottom, which flares into a widened portion 12*e*, known as the columella.

Protrusions 10*c* of the dilator's legs can have many shapes and configurations, as will be discussed. Note that protrusions 10*c* extend inwardly from legs 10*b* and overlie the upward surfaces of columella 12*e* and may or may not contact the columella, depending upon the degree of insertion, the geometry of the user's nose, and the distance between bight portion 10*a* and protrusions 10*c*.

Note that no portion of legs 10*b* contacts septum 12*d* above columella 12*e* and thus the legs do not exert any squeezing pressure on septum 12*d*.

Dilator 10 preferably is made from a flexible, resilient plastic material such as polycarbonate, rubber, silicone, hydro-gels, fiber reinforced composites although other materials such as metal and wood, or a combination of plastic, metal, or wood or any other suitable material or combination can be used. If plastic is used, it can be either a thermosetting (such as polycarbonate) or a thermoplastic material (such as methyl methacrylate polymer). In the case of a thermoplastic material, a user can either manually manipulate the device without heat by applying enough force to cause the material to reach a plastic state where it can be briefly adjusted and when said force is terminated the material solidifies to the form applied, and/or heat can be applied to the dilator to its plastic temperature, then more easily manually alter its shape for a custom fit. In addition, the plastic material can optionally be porous in order to prevent occlusion of air and moisture from reaching and leaving the nasal lining. Pores in the plastic material can optionally be pre-filled with odorants and/or medications.

Due to the variations in nose sizes of humans, the dilator may be made in three sizes.

E.g., for a user with a Large Nose the overall dimensions of the dilator are preferably as follows: Height: 1.25", Width (left to right in FIG. 2A): 1.00", and Depth (left to right in FIG. 2C): 0.63".

For a Medium Nose the three dimensions are 1.00"×0.80""×0.50".

For a Small Nose the three dimensions are 0.81"×0.64"×0.41".

Of course, more than three sizes as well as custom-fitted sizes may be provided.

The overall dimensions of the locking or retention (columella) section of the dilator for a user with a Large Nose are preferably as follows: Height (top of bight (inside of "U"), to center of protrusion): 0.30", Width (left to right, inside leg to top of protrusion, in FIG. 2A): 0.06", and Depth (left to right in FIG. 2C): 0.19".

For a Medium Nose the Height, Width, and Depth are 0.24"×0.05"×0.15".

For a Small Nose the Height, Width, and Depth are 0.19"×0.04"×0.12".

Any of these three columella retention section sizes may be provided for each of the three overall sizes in the previous paragraph. More than three columella sizes, including custom-fitted sizes, may be provided.

Installation and Use—FIG. 1

The wearer inserts arms 10*j* into respective nostrils 12*a* until bight portion 10*a* of the dilator contacts the bottom surface of columella 12*e*. The distance between protrusions 10*c* on legs 10*b* is less that the width of columella 12*e*. However, due to the flexibility and elasticity of dilator 10, during insertion the bottom surface of columella 12*e* will cam the upper sloped surfaces of protrusions 10*c* outwardly to a wider separation (not shown) so that legs 10*b* will spread slightly further than indicated (not shown) so that the protrusions will easily pass over columella 12*e*.

After the dilator is inserted far enough that protrusions 10*c* pass the columella, the legs will close to the separation shown, so that the protrusions overlie the upper surface of the columella, as also shown. The positions overlie the columella to ensure that the dilator will not fall out of or be unintentionally ejected from the nose, e.g., due to sneezing, running, eating, coughing, sleeping, etc. Thus, the protrusions constitute retention means that overlie the shoulders of a user's columella without exerting any pinching or horizontal force against the user's septum to resist withdrawal of the dilator from the user's nostrils without pinching the user's septum.

Prior to insertion, or during the insertion process, the wearer may adjust the bends or curvature of the legs of the dilator so that they fit comfortably around the columella and press the outer sides of the nostrils out sufficiently so that the wearer can breathe freely. I.e., the tips 10*d* of the arms will cam or spread the sides of the nostrils from their normal, relaxed position 12*c* to their expanded or dilated position 12*b* to facilitate breathing, which is the dilator's normal function. Such dilation and breathing facilitation will reduce or eliminate snoring, obstructive sleep apnea (temporary cessations of breathing), and xerostomia as well as reduce congestion, reduce mouth breathing and dry mouth, improve restful sleep, reduce stress, improve oxygen flow into the lungs and improve expelling of carbon dioxide, improve athletic performance, and improve mental clarity, etc.

When the user desires to remove the dilator, they merely pull down bight portion 10*a*, causing the top surface of columella 12*e* to cam the lower surface of protrusions 10*c* outwardly, causing the protrusions and the legs of the dilator to spread (not shown) to allow the dilator to be withdrawn. Bight portion 10*a* may have an optional handle (not shown) attached to it to facilitate grasping for removal. When the dilator is withdrawn, tips 10*d* of arms 10*j* move down, allowing the sides of the user's nose to return to their undilated and resting position 12*c*.

The dilator material, while rigid, has an elastic or spring-like nature and certain components or sections can be modified to change the form, structure, and orientation of the shapes. When the dilator is bent sufficiently from its original form, the dilator will maintain its new shape when made from the suggested materials above. By manually applying enough force to a part or section of the dilator, the material will reach a plastic state in which the part or section can be repositioned. Once repositioned, the material becomes firm or rigid again and the material now holds the new position and form due to its material memory. If a force is applied to the part or component up to a predetermined extent, i.e., it is bent up to a predetermined degree, the spring-like properties of the material will return the part or component to its original position or, if the part was modified in shape or form, it will return to its the last formed position. The bight, legs, arms, and pads can all be manipulated in a symmetrical or asymmetrical manner, allowing the user to optimize the fit of the dilator to their unique nasal anatomy.

The material can be manually adjusted or adjusted with various tools and/or made more pliable with warm water or with warm air and then it can be adjusted more easily. As it cools or is left in a rested state it will retain its rigid state or form, yet will remain spring-like in its the newly formed position.

This dilator has wide, smooth radii and broader contact areas where needed to aid in securing the device in the nasal anatomy as well as optimizing the pressure due to the force applied to the nasal anatomy. Increasing the area of the smooth parts that contact the nasal anatomy will reduce the pressure and potential pain and discomfort as well as increasing the surface area in contact with the nasal anatomy to improve retention of the dilator. The wide, smooth radii and gentle forms further minimize pinching, sharp edges, or other potential discomfort for the user.

Human noses generally have similar angular forms but have a wide range of sizes, angles, and curves, even within the approximately 13-19 classified types or forms. According to Prof. Abraham Tamir of Ben Gurion U., Israel, the majority of nose shapes can be classified into one of 14 distinct types. Journal of Craniofacial Surgery, 2011. Since his initial study and classification, others have distilled the figure of most common nose types to 12 distinctive nose types. Nose shapes are defined by a variety of factors, primarily the shape of the nasal bones and the nasal cartilage. The twelve most common nose forms classified are: 1) Fleshy; 2) Turned-up (or Celestial Nose); 3) Roman; 4) Bumpy; 5) Snub; 6) Hawk; 7) Greek; 8) Nubian; 9) East Asian; 10) Nixon; 11) Bulbous; 12) Combo. By example, and not limitation, Fleshy Noses are "identified by their large, protruding shape. They can be petite as well, just so long as they have more of a fatty appearance than a bony one." Another sample definition presented is the Roman Nose described as "Much like the less-common Greek nose, the Roman nose is named so because it resembles the noses found on the faces of many ancient Roman sculptures. The Roman nose is marked by its sloping curve that prominently protrudes from the face. Its exaggerated bridge often has a slight bend or curve.

Size is the primary variable of all nose forms. The dilator has three sizes as stated, but may have other sizes and custom sizes.

Another variance in the anatomy of noses is the nostril size and position or rotation. Generally, nostrils are either more parallel (FIG. 7A) and perpendicular or normal to the face or they are more angled (FIG. 8A), in which case the nostrils angle toward each other and the closer the forward end of the nostrils is to the tip or forward point of the nose, the more they form a "V", with the point of the "V" being toward the tip of the nose.

Figure 12A:
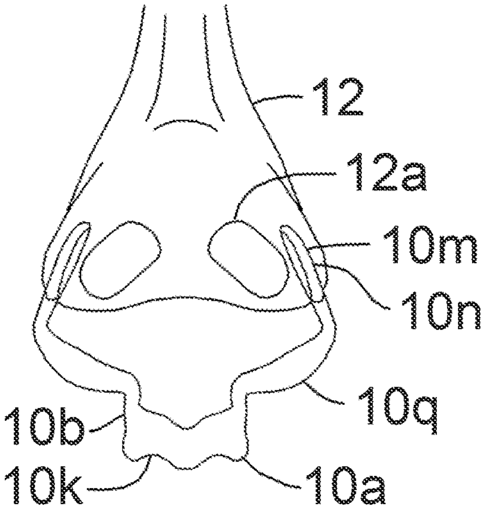
FIG. 12A is a view from the front below of a nose with a dilator being inserted, with the dilator in a wide position

Other core variables include, but are not limited to, the columella which is the wider flesh and cartilage section of the nose between the nostrils, which extends upwardly into the nose and reduces in width to form a top shoulder as it narrows and joins the septum (FIGS. 1, 12*e* transition to 12*d*), the cartilage between the left and right nasal airways.

The nasal dilator in this design accommodates the size and width of columella 12*e* between the nostrils with the variable size offerings in which bottom section or bight 10*a* of the "U" shape varies in width with each size, thereby moving the vertical sections or legs 10*b* further apart or closer together as needed to optimize fit into the nostrils.

Figure 11A:
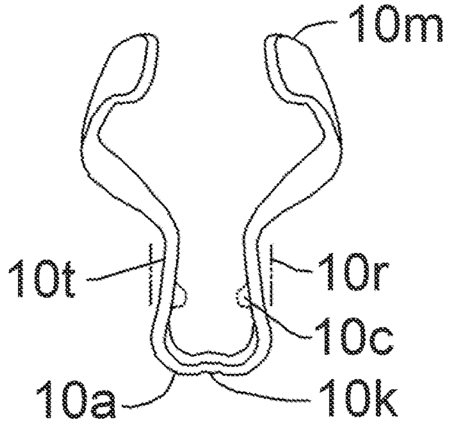
FIG. 11A shows a front elevational view of the dilator with the legs and their protrusions bent inwardly. The phantom lines show the generally vertical position of the dilator prior to adjustment of the legs and protrusions.
Figure 11B:
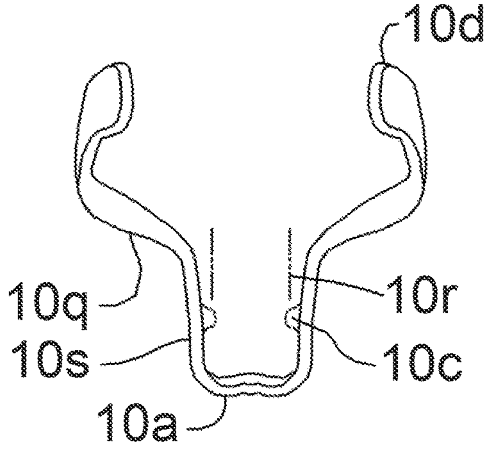
FIG. 11B shows a front elevational view of the dilator with the legs and their protrusion bent outwardly. The phantom lines show the generally vertical position of the dilator prior to adjustment of the legs and protrusions.

The width and height of the columella 12*e* and septum 12*d* can vary. Legs 10*b* on each side of the bottom or bight section 10*a* extend upwardly into the nose in various sizes. Alternate embodiments include a horizontal protrusion or retention shelf 12*c*. Its size and location can engage the top shoulder of columella 12*e* to resist unwanted removal of the dilator during sleep, exercise, sports, or any other user activity. Vertical sections 10*b* with or without this embodiment of horizontal protrusion 10*c* can be adjusted inwardly toward columella 12*e* and septum 12*d* to make a tighter or more secure fit (FIG. 11A). Also legs 10*b* and associated horizontal protrusion 10*c* in those embodiments can be adjusted outwardly from columella 12*e* and septum 12*d* to enlarge the gap between the legs for a less constricted fit (FIG. 11B). Legs 10*b* are adjusted using a pivot point generally located in the curved transition from bottom or bight section 10*a* to the respective legs 10*b* to allow the legs to move inwardly or outwardly from the original generally vertical position.

The diameter and height of a user's nasal airway from the nostril extending upwardly into the nose can vary as well. The vertical sections are wide and flattened (FIG. 2C) to provide a wider surface area along the septum to counter the spring-like force being applied by the arm and pad against the outer wall of the nose.

An arm or upper section 10*j* continues from the top of legs 10*b* and forms an upward and rearward curve designed to extend around the rear of the curved nasal airway. Arm 10*j* holds pads 10*d* atop the arms in a higher position and along outer nasal wall 12*b* while keeping the dilator's structure along the back edge of the nasal airway and maintain a maximally clear nasal airway for the greatest possible volume of unobstructed air flow.

Figure 12C:
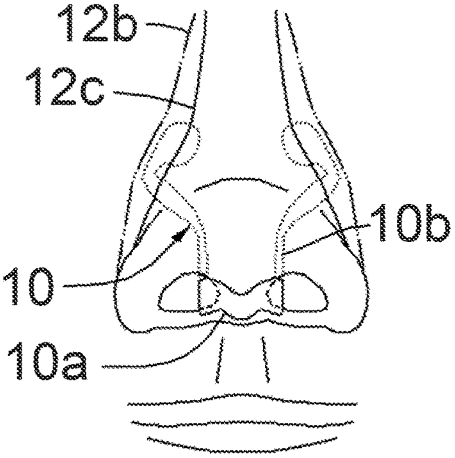
FIG. 12C is a front elevational view showing the dilator placed in the nose.
Figure 12B:
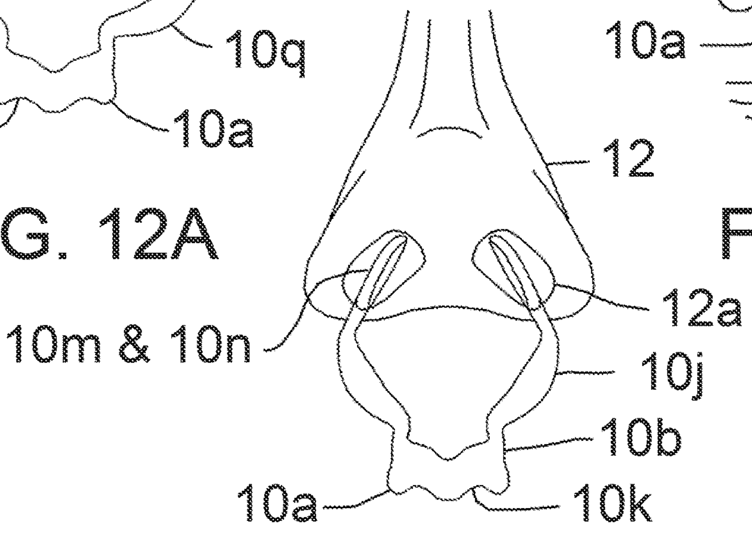
FIG. 12B is a view from the front below of a nose with a dilator being inserted, with the dilator pinched down to illustrate a method for facilitating placement of the dilator in the nose.

Arm 10*j* or 10*q* (FIG. 10A) can bend outwardly and downwardly slightly to extend nasal pads 10*d* and 10*m* (FIG. 10B) further from the centerline of the dilator. The bend of arm 10*j* can be pivoted generally at the top of log 10*b*, thereby applying greater outward pressure to the outer wall of the nose and increasing the volume of the nasal airway (FIGS. 1 and 12C). Applying greater pressure on the outer wall of the nose also provides greater retention of the dilator in the nose as the spring-like force is applied outwardly to the outer wall of the nose and inwardly along the flat surface of legs 10*b*. Each side opposing the other to balance the forces in a static and equal balance.

Pads 10*d* located at the top of arms 10*j* have large generally flat but slightly radiused convex surfaces that are designed to contact the outer wall of nose 12*c* and apply pressure to force them to position 12*b* to open the nasal airways and improve breathing performance. The pads transition to the arms 10*j* below and the pads are initially generally parallel with leg sections 10*b* below positioned along septum 12*d* and located inward of pads 10*d*. The pads have three primary adjustments with infinitely variable positions between them all with their extents of possible range of motion made possible by their geometry and the material used. These adjustments all utilize a similar pivot zone which it typically located in the transition from the pad to the upper portion of the arm.

The adjustment available to these forms on the dilator can provide a user with a standard-no-adjustment-needed fit to a highly customized fit. The sections that can be adjusted are, but are not limited to, bight section 10*a*, which in some embodiments may have notches (FIGS. 7B and 8B, 10*k*) with one notch in the front of the bight section and two notches along the rear edge of the bight section; the legs on each end of the bight section; the arms, and pads 10*d*, which have a multitude of infinitely variable adjustments within the range of extents for each component.

Figure 10A:
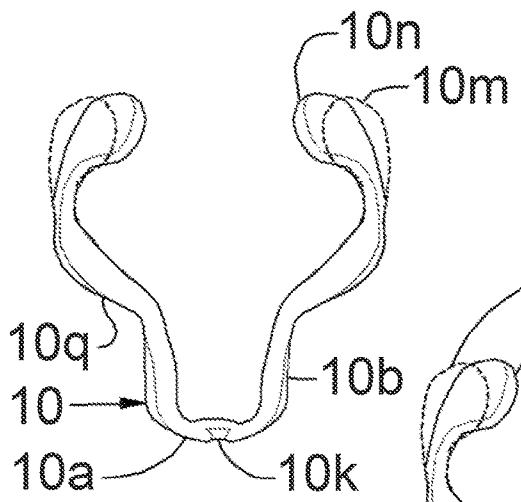
FIG. 10A is a front elevation view showing the arms and pads of the dilator being moved outwardly.
Figure 10B:
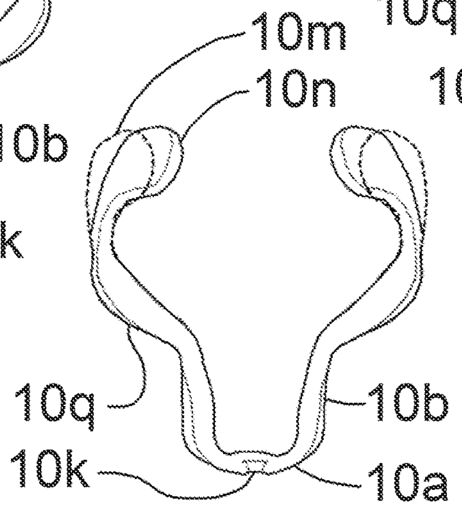
FIG. 10B is a front elevation view showing the arms in the outwardly adjusted position of FIG. 10A, but with the pads being readjusted to re-align with the angle and side slope of the nose.

The adjustments of the entire dilator structure include, but are not limited to, the rotation of the entire structure including the bight section, the legs on each end of the bight section, the arms above each leg and the pads to a generally angled or "V" shape from the parallel or "U" shape. If a user has parallel nostrils (FIG. 7A, 12*f*) then the adjustment of the dilator structure may not be necessary. However, if the user has angled nostrils (FIG. 8A, 12*g*) they will benefit from the rotation modification of the dilator structure shown in the before position (FIG. 7B) with the bight section and associated dilator structure above it in a generally horizontal position with the balance of the dilator structure as shown in FIG. 1, with the legs parallel and the arms and pads above the arms parallel to the centerline of the dilator and nose. By holding the dilator at its rear and pinching each leg between the user's fingers and rotating the back of the legs outwardly and the front of the legs inwardly, the entire dilator can be rotated about the centerline of the bight section as shown before bending at 10*a* (FIG. 7B) and after bending at 10*a* (FIG. 8B). This results in the compression of the single notch (FIG. 8B, 10*k*) at the front of the bight section and expansion of the two notches at the back of the bight section (FIG. 8B, 10*a*). This in turn rotates the angle of each leg inwardly, creating a "V" shape for the dilator in lieu of the "U" shape that the dilator had prior to the rotational adjustment of the dilator. Since the legs in each end of the bight section rotate inwardly with this adjustment, the arms and the pads all rotate with the legs and bight section. Thus the entire structure is rotated inwardly at the front and outwardly at the rear to bring the bight section, legs, arms, and pads into a general alignment (FIG. 8B) with the angled nostrils (FIG. 8A) of a user. This structure adjustment will start to optimize the fit, comfort, breathing performance and retention of the dilator for users with angled nostrils. This primary form modification of the structure can effectively modify the angle of the pads sufficiently, such that the next adjustment (rotation of the front of the pads) may not be required.

Figure 10C:
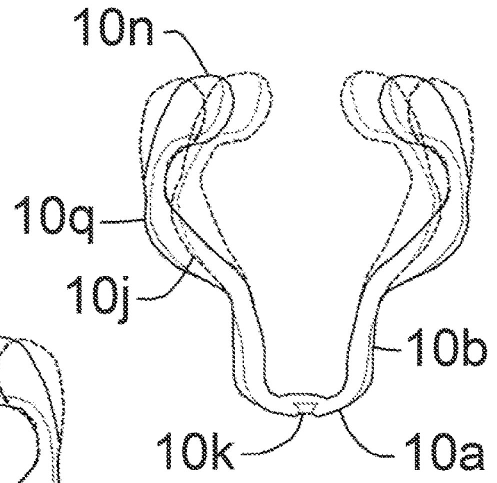
FIG. 10C is a front elevation view showing the various positions of the adjustments if FIGS. 10A and 10B in sequence. The innermost dashed position of arms and pads reflect the adjustments from FIGS. 9A and 9B for the rotation inward and side tilt adjustments respectively, to the outermost dashed image in FIG. 10C, which shows the arms bent outwardly from the adjustments in FIG. 10A. The center and final solid line position in FIG. 10C shows the pads being adjusted as reflected in FIG. 10B to realign them for the angle and side slope of the user's nose.

The adjustments to the legs, and on some embodiments the retention shelf or protrusions 10*c* include, but are not limited to:

1) Rotation of the legs to orient the legs so they are parallel or close to parallel with the columella and/or septum and/or nostrils;
2) Bending the legs inwardly from their original position (FIG. 11A, 10*r*), thereby tightening the fit for both legs and for the embodiments with the nasal retention shelf protrusions (FIG. 11A, 10*c*) as these components can obtain a better friction fit on the septum and/or provide better engagement for the retention shelf protrusion (FIG. 11A, 10*c*) on the upper shoulder of the columella (FIG. 1, 12*e*);
3) Bending the legs (FIG. 11B, 10*s*) outwardly from their original position shown 10*r* relaxes the fit for both legs 10*s* and for the embodiments with the nasal retention shelf protrusions as these components can reduce the friction fit and/or impingement on the septum and/or reduce any impingement from the retention shelf protrusion on the upper shoulder of the columella.

Figure 7A:
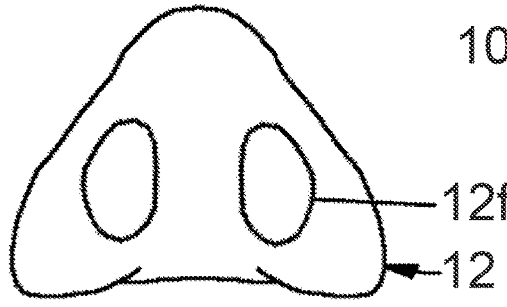
FIG. 7A is a bottom view of a typical human nose with parallel nostrils.
Figure 8A:
FIG. 8A is a bottom view of a typical human nose with angled nostrils.
Figure 7B:
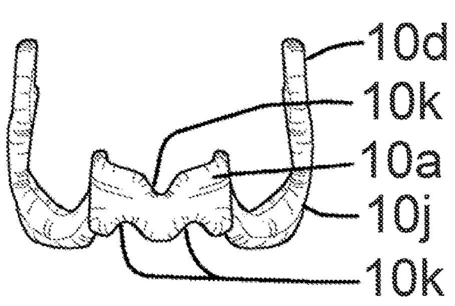
FIG. 7B is a bottom view of a dilator with various elements and components of the dilator and various methods of adjustment to facilitate improved fit, comfort, breathing performance, and retention. This dilator is suitable for placement in the nose of FIG. 7A.
Figure 8B:
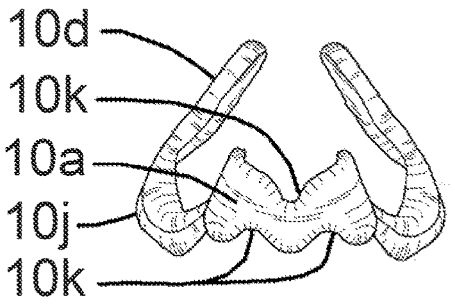
FIG. 8B is a bottom view of a dilator with various elements and components of the dilator and various methods of adjustment to facilitate improved fit, comfort, breathing performance, and retention. This dilator is suitable for placement in the nose of FIG. 8A.
Figure 9A:
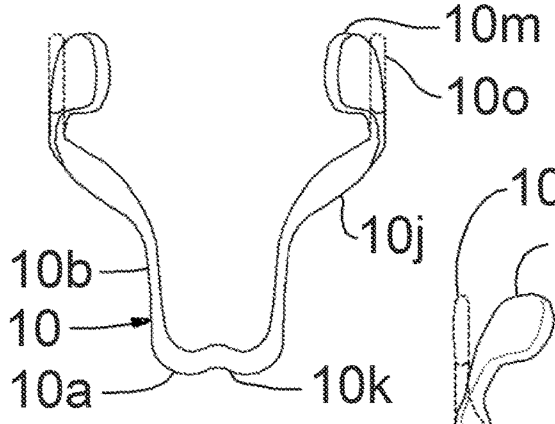
FIG. 9A is a front or elevational view of a dilator like FIG. 1 showing a possible adjustment of the pads by inward rotation.
Figure 9B:
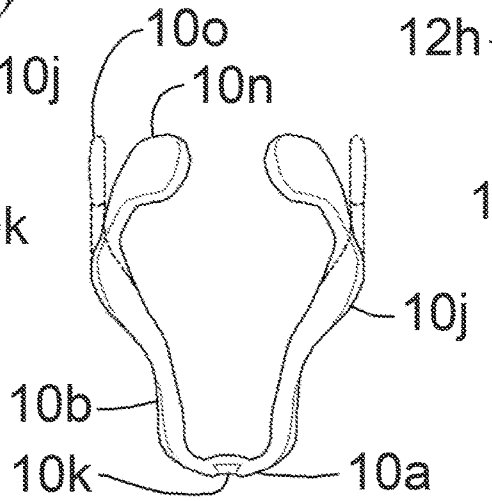
FIG. 9B shows a similar front or elevational view showing a possible adjustment of the pads once rotated inwardly as shown in FIG. 9A, with a side tilt of the pads inwardly to align with the side slope of the nose.
Figure 9C:
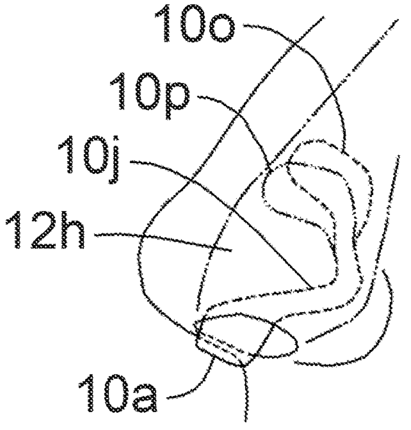
FIG. 9C is a partially sectional side view of a dilator like FIG. 1 placed in a nose and showing two ghosted vertical tilt positions of the dilator's pads.

The adjustments to the arms and include, but are not limited to:

1) Bending the arms outwardly from a pivot point at the bottom of the arm at the transition to the leg, causing the arms and the pads to move outwardly from the centerline of the dilator and the nose. This expansion of the position of the arms and pads results on a greater outward or opening force applied to the outer walls of the nose, thereby increasing the volume of the nasal airways by up to 45% or more and improving the volume of airflow and the oxygen and carbon dioxide exchange with the lungs. This outward pressure also improves the friction hold and surface area contact of the pad on the outer nasal wall thereby improving the retention of the dilator in the user's nose.
2) Bending the arms inwardly, reduces the outward pressure on the outer nasal walls from the arms and the pads and can improve the comfort for some users if the pads are exerting too much pressure on the outer wall of their nose;

The adjustments to the pads include, but are not limited to:

1) Rotation of the front of the pads (FIG. 1, 10*d*), inwardly and outwardly (FIGS. 9A, 10*o* and 10*m*) They are shown rotated inwardly, so the front of the pad (FIG. 2C, 10*d*) with the left edge of 10*d* defined as the "front" of the pad, can be aligned with the general angle of the nose and/or nostrils (FIGS. 7A and 8A). If the front of the pads are rotated inwardly (FIGS. 9A, 10*o* and 10*m*) the pads can be aligned with the unique angle of the user's nose or nostrils (FIG. 8A). In some cases, the nostrils and bottom of the columella are generally parallel (FIG. 7A), but the outer nasal walls have an angle outside and above the nostrils such angle is formed by the widest part of the nose at the bottom of the nose converging at the tip of the nose (FIG. 7A). This adjustment, the rotation of the pads inwardly (FIGS. 9A, 10*o* and 10*m*) provides the user with the ability to match the angle of the pads to their unique size, shape and angle of their nose;
2) Side tilt of the top edge of the pad (FIG. 1, 10*d*); the pad can be tilted inwardly or outwardly (FIGS. 9B, 10*o* and 10*n*). The top edge of the pad can be tilted inwardly to create a cross slope for the pad (10*n*), in conjunction with the angle of the pad from the prior adjustment (FIG. 9A, 10*m*). Thus, the side slope of the pad can be adjusted to match the side slope of the outer wall of the nose (FIG. 9B, 10*n*). The side slope of the nose is the slope from the ridge or centerline of the nose down the outer wall of the nose to the face or cheek. The side slope of the nose varies as it progresses upwardly from the tip of the nose toward a point between the eyes since the length of the side slope or distance from the face or cheek to the ridge of the nose reduces the further up the nose as the transition from the ridge of the nose to the face reduces in length; and
3) Vertical tilt of the front of the pad up or down to enhance outward pressure on the nasal wall and/or avoid conflict with anatomical conditions in the nose. This will optimize the fit and performance of the dilator and the pad in the user's nose (FIGS. 9C, 10*o* and 10*p*).

All of the adjustments to the pads above may be tuned as needed if the bight, the legs, 10*b*, and the arms below these pads are adjusted. This allows the user to adjust fit and pressure of the device and then re-tune the pads to align them for the angle of the nose and the side slope of the nose for maximum surface contact along the side walls of the nose to optimize fit, comfort, breathing performance and retention.

The variety and range of adjustments available for this dilator and the associated components of the dilator (bight, legs, arms, pads) will optimize comfort, fit, breathing performance and retention. The surface and planar modifications of the component parts allow individual users the ability to adjust each element of the dilator to fit their unique nasal anatomy and maximize contact of the surface areas of legs on the columella and septum, arms, and pads on the outer wall 12*b* of the nose. This will optimize the enlargement and opening of the nasal airways, enhance retention and reduces pressure from the applied force of the spring-like action applied by the dilator to the outer wall of the nose, resulting in less pain, and more comfort:

1) Matching the angle of the pad with the form of the tapering nose from the face to where the nostril flares to the tip of the nose (FIG. 9A).
2) Matching the side tilt of the pad to match the side slope of the outer nasal wall (FIG. 9B).
3) Matching the vertical tilt of the pad (FIG. 9C) to optimize comfort and fit.

The bight, the vertical sections or legs, the arms, and pads all have multiple adjustment opportunities and provide infinitely variable adjustability within the range of the extents of the adjustments available. Adjustments can be made symmetrical or asymmetrical to accommodate each user's unique nasal anatomy.

Placement of the internal nasal dilator, with none, some, or all of the various adjustments defined can be accomplished in generally the same manner. The user should adjust the dilator to align the pads with the angle and slope of the nostrils (FIG. 12A) and adjust arms 10*q*) so as to position pads 10*m* and 10*n*) to a position just outward of each nostril. By holding the dilator between the user's thumb and forefinger at the vertical sections or leg, the user can pinch the legs together such that the legs, the arms, and the pads narrow in position toward each other and the centerline of the device sufficiently to align the pads with the nostrils. This in turn generally aligns the arms and legs below with the nostrils as well. Once aligned, the user can place the dilator into the nose and until the top of the bight section engages the bottom of the nose between the nostrils at the columella. Then the user can release the pinched legs and the legs, arms, and pads will expand outwardly inside the user's nose, applying an outward pressure to the original position of the outer wall of the nose and moving the outer walls of the nose outwardly to enlarge the nasal airways by up to 45% or more and improving airflow and breathing performance as well as retention of the dilator.

FIGS. 2A to 6B—Specific Embodiments

As stated, protrusion 10*c* of FIG. 1 may have various configurations, which are shown in FIG. 2*a* through 6*c*. The dilator of FIG. 2 has a generally semispherical projection; in FIG. 3 it has an elongated projection with rounded form and ends, in FIG. 4 it has an elongated projection with radiused forms including the ends and sloping slides, in FIG. 5 it has a thicker cam shaped leg with an upwardly tapering undercut, and in FIG. 6 it has a thicker sloping or ramping leg with a horizontal undercut. In each set of figures, the "A" figure is a front or elevational view of the dilator, the "B" figure is a perspective view from above and to the right, and in the "C" figure is a cross-sectional view taken along the lines indicated by the C-C sectional designation lines in the "A" figure Specifically, protrusion 10*e* of FIG. 2 has a generally semi-spherical shape with a truncated top to provide a broader contact area for less pressure in case the user lies on a side and presses the dilator out of position The semi-sphere also has a sloping flat vertical surface atop the semi-sphere to form a ramp or cam to facilitate insertion past the columella. The base of the semi-sphere has a circumferential radiused fillet or ramp that has a gradual slope from the leg's surface up to the side of the semi-sphere.

Some of the advantages of the semi-spherical shape include the spherical form with radius fillets to the leg produces a sufficient retention shelf over the shoulder of the columella to resist withdrawal, while minimizing the material needed to create the retention shelf. Since the spherical form (FIGS. 2A-C) offers the least amount of extended material contained in the protrusions and the form is rounded and/or truncated (FIG. 2*b*, 10*e*) to soften the form, it creates the most advantageous form that can still present a shelf form (FIG. 2A, 10*e*) to engage the upper shoulder of the columella for improved retention, while minimizing the protrusion from engaging or causing pain to the columella and/or septum. Further the reduction in material needed in this form over other forms reduces or eliminates hard edges, sharper corners or other additional structure that may result in a conflict with the widely varied internal anatomy of the nose and nose types, which could result in discomfort or pain to the user, which the spherical form improves. In addition, when a downward or extraction force is applied, the dilator starts to move down, and the skin and cartilage of the columella naturally form or wrap around the bottom edge of the sphere. This results in greater contact area between the columella and the dilator and improves resistance to removal as needed. It also minimizes contact and potential pain or conflict with the columella and/or septum while in the resting state during normal use. During intentional extraction or removal and with sufficient removal force, the spherical shape will allow the protrusions to cam off the shoulders of the columella to enable removal.

The spherical shape further reduces conflict since the size of the spherical form can be minimal while still achieving the objective of retention. The reduced form, size, and shape minimizes potential conflict with the anatomy of the nose as the internal volume of the nose becomes more constricted at the tip of the nose. For a wide range of nose shapes and sizes this form also reduces the edges or corners of other forms such as in FIG. 6A, element 10*i* by example, but not limitation, that may apply undesired pressure or pain on the septum and/or columella and/or any other forms of the nasal anatomy at the constricted tip of the nose.

While the design is intended to avoid contact with the septum (FIG. 1, 12*d*), side pressure or force may be applied during certain uses, such as sleeping if a pillow applies side pressure on the nose, as one example, which may translate to the retention shelf or protrusion and the septum. The spherical or truncated sphere form reduces the force and associated pressure and possible pain from such contact with its minimal size, rounded forms, and the optional flat contact area of the truncated top of the spherical form. This provides a larger contact area or a wider pad in case such contact with the septum occurs. Thus, it reduces the point pressure and associated possible pain over the higher forces and greater potential pain that may be applied by a smaller contact area since Pressure=Force/Area.

The sloped ramp or cam on the top of the spherical form and radius fillets that transition the sphere to the leg apply less pressure on the nasal anatomy during insertion as the top of the sphere provides a larger surface area to contact the nasal anatomy as the dilator is inserted and the protrusions contact the columella and septum during insertion. As with the top of the sphere sliding on the columella and septum, the leading edge is enlarged to reduce pressure from the force applied during insertion.

The outer edge of the ledge of each protrusion is flattened and has radius edges that transition to rounded or spherical forms at the top and bottom edges so that it will reduce contact area along the outer edge. Also it will not create a sharp edge should it contact the septum or columella and it will ride smoothly over the columella as the spherical top and bottom edges 10*e* when the dilator is inserted or withdrawn from the nose.

Protrusion 10*f* of FIG. 3 has an elongated configuration so that it extends the full width of leg 10*b*. It has rounded ends and rounded or curved lateral sides (top and bottom) so that it has a generally half-capsule configuration. The outer edge of the ledge of each protrusion 10*f* is rounded so that it will not create a hard edge should it contact the septum or columella and ride smoothly over the columella when the dilator is inserted or withdrawn from the nose.

Protrusion 10*g* of FIG. 4 also has an elongated configuration that it extends for a portion of the width of leg 10*b*. However, it has tapering top and bottom sides and utilizes radius fillets where connected to leg 10*b*. Protrusion 10*g* of FIG. 4 also has an elongated configuration so that it extends the full width of leg 10*b*. However, it has flat ends and tapering top and bottom sides. The outer edge of the ledge of each protrusion 10*g* is rounded so that it will not create a hard edge should it contact the septum or columella and ride smoothly over the columella when the dilator is inserted or withdrawn.

Protrusion 10*h* of FIG. 5 also has an elongated configuration that extends for the full width of its leg. However, each leg 10*b*' has a longer thickened midsection forming a cam shape from the upper portion of the vertical portion of the leg that continues to the outermost extent or height of protrusion 10*h*. Thus protrusions 10*h* have no top surface but each has an undersurface that slopes back to its leg as indicated. The cam shape facilitates a smooth transition for the protrusion so it will ride smoothly over the columella when the dilator is inserted. The outer edge of the ledge of each protrusion 10*h* is rounded so that it will not create a hard edge should it contact the septum or columella and it will ride smoothly over the columella when the dilator is withdrawn.

Protrusion 10*i* of FIG. 6 also has an elongated configuration that extends for the full width of its leg. Each leg 10*b*" has a longer thickened midsection, forming a ramp or wedge shape from the upper portion of the vertical leg that continues to the outermost extent of projection 10*i*. Thus projection 10*h* has no top surface but its undersurface is horizontal or substantially normal to the inside surface of its leg to form a downwardly facing ledge as indicated. The outer edge of the ledge of each protrusion 10*i* is rounded so that it will not create a hard edge should it contact the septum or columella and ride smoothly over the columella when the dilator is withdrawn.

CONCLUSION, RAMIFICATIONS, AND SCOPE

The embodiments of the dilator shown provide useful and advantageous features. The dilator can be made inexpensively, it can be installed by the untrained wearer, it is rugged, unobtrusive, and disposable, yet it resists unintentional withdrawal without creating painful pressure on the user's septum.

While the above description contains many specificities, these should not be considered limiting but merely exemplary. Many variations and ramifications are possible. For example, the protrusion can have other shapes so long as it is able to overlie the top of the columella to provide a barrier to withdrawal and so long as its inwardly facing surfaces are sloped adequately to be inserted and withdrawn past the columella. The legs of the dilator need not be flat or ribbon shaped and can have many other shapes than indicated, including most of those of the above '512 Brown et al. patent. The dilator can be supplied in any color, or in a combination of colors or may be translucent with blended colors, or may be clear (absence of color). Lubrication can be applied to the dilator to facilitate insertion. The dilator can be supplied in or adjusted to non-symmetrical shapes to accommodate noses with non-symmetrical or oversize or undersize nostrils. The vertical sections of the legs of the dilator may have other shapes with different curvatures.

While the present system employs elements, which are well known to those skilled in the art of nasal dilator design, it combines these elements in a novel way which produces a new result not heretofore discovered. Accordingly, the scope should be determined, not by the embodiments illustrated, but by the appended claims and their legal equivalents.

I claim:

1. A nasal dilator configured to be inserted into a user's nostrils for dilating said nostrils to facilitate breathing and increase the volume of airflow, where said user has a nasal septum having a bottom or lower end terminating in a columella having a bottom surface and a pair of shoulders facing upwardly in said user's respective nostrils, comprising:

(a) an elongated, flexible, elastic member having a generally U-shaped configuration with two upwardly extending sides, each upwardly extending side having a top section comprising an arm and a bottom section comprising a leg, and a bottom base section connecting said bottom ends of said legs and having a bottom side and a top side, each leg having an inside surface facing the other leg and an outside surface facing away from the other leg, (b) said bottom base section having a top side facing upwardly and a bottom side facing downwardly when the legs of said U-shaped member are inserted into the user's respective nostrils, (c) said upwardly extending sides each being (1) substantially longer than said bottom base section, (2) generally vertically oriented, (3) having a free upper end with a widened portion or pad on its outside surface, and (4) shaped and sized so that when said upwardly extending sides are inserted into the respective nostrils of the user having a nose anatomy within a predetermined range of sizes, said top side of said bottom base section will contact said bottom surface of said user's columella and each of said widened portions or pads at the upper end of each arm will engage and urge an outer side of its respective nostril outwardly to dilate said nostril, (d) each of said legs having a protrusion extending toward the other leg, said protrusion having an underside spaced from said top side of said bottom base section by a predetermined distance so that when the sides of said U-shaped member are inserted into the respective nostrils of the user having a nose anatomy within a predetermined range of sizes and said top side of said bottom base section contacts said bottom surface of said user's columella, said underside of said protrusion will overlie an upper side of said user's columella so as to cause said dilator to resist withdrawal from said user's nostrils, and (e) each of said legs and said protrusion being shaped and sized so that they do not exert any pinching or horizontal force against said user's septum, the other leg, or the other protrusion, whereby said dilator will resist withdrawal from said user's nostrils;

wherein said protrusion has a semi-spherical shape with a truncated top surface.

2. The nasal dilator of claim 1 wherein said U-shaped member is made of a material selected from the group consisting of plastic, metal, wood, rubber, silicone, hydrogels, fiber reinforced composites or a combination thereof.

3. The nasal dilator of claim 1 wherein each leg extends up from said bottom base section at a generally right angle and parallel to and spaced from the corresponding portion of the other leg.

4. The nasal dilator of claim 1 wherein each arm also slopes outwardly, away from the corresponding portion of the other arm, and then extends up vertically to the free upper end.

5. A nasal dilator configured to be inserted into a user's nostrils for dilating said nostrils to facilitate breathing and increase the volume of airflow, where said user has a nasal septum having a bottom or lower end terminating in a columella having a bottom surface and a pair of shoulders facing upwardly in said user's respective nostrils, comprising:

(a) an elongated, flexible, elastic member having a generally U-shaped configuration with two upwardly extending sides, each upwardly extending side having a top section comprising an arm and a bottom section comprising a leg, and a bottom base section connecting said bottom ends of said legs and having a bottom side and a top side, each leg having an inside surface facing the other leg and an outside surface facing away from the other leg, (b) said bottom base section having a top side facing upwardly and a bottom side facing downwardly when the legs of said U-shaped member are inserted into the user's respective nostrils, (c) said upwardly extending sides each being (1) substantially longer than said bottom base section, (2) generally vertically oriented, (3) having a free upper end with a widened portion or pad on its outside surface, and (4) shaped and sized so that when said upwardly extending sides are inserted into the respective nostrils of the user having a nose anatomy within a predetermined range of sizes, said top side of said bottom base section will contact said bottom surface of said user's columella and each of said widened portions or pads at the upper end of each arm will engage and urge an outer side of its respective nostril outwardly to dilate said nostril, (d) each of said legs having a protrusion extending toward the other leg, said protrusion having an underside spaced from said top side of said bottom base section by a predetermined distance so that when the sides of said U-shaped member are inserted into the respective nostrils of the user having a nose anatomy within a predetermined range of sizes and said top side of said bottom base section contacts said bottom surface of said user's columella, said underside of said protrusion will overlie an upper side of said user's columella so as to cause said dilator to resist withdrawal from said user's nostrils, and (e) each of said legs and said protrusion being shaped and sized so that they do not exert any pinching or horizontal force against said user's septum, the other leg, or the other protrusion, whereby said dilator will resist withdrawal from said user's nostrils;

wherein each of said legs has inside and outside surfaces and a pair of edges connecting said inside and outside surfaces so as to define the widths of said inside surfaces, each protrusion having an elongated shape and having the same width as said inside surfaces so that each protrusion extends to said pair of edges, each protrusion having top and bottom lateral sides that taper to said inside surface of its respective leg.

6. The nasal dilator of claim 5 wherein each protrusion has an elongated curved or cam shape, and each leg has a portion of its inside surface above its protrusion that has the same height as its protrusion so a top surface of the protrusion is defined by the inside surface of the respective leg.

7. The nasal dilator of claim 5 wherein an elongated ramp, slope or wedge shape and said-bottom lateral side or undersurface of each protrusion extends normal to said inside surface of its respective leg.

8. The nasal dilator of claim 7 wherein each elongated member has a portion of its inner sidewall above its protrusion that has the same height as its protrusion so the top surface of the protrusion is defined by an inner surface of the elongated side.

9. A nasal dilator configured to be inserted into a user's nostrils for dilating said nostrils to facilitate breathing and increase the volume of airflow, where said user has a nasal septum having a bottom or lower end terminating in a columella having a bottom surface and a pair of shoulders facing upwardly in said user's respective nostrils, comprising:

(a) an elongated U-shaped flexible member having a substantially flat bottom or bight section with a front edge and a back edge and two elongated sides that extend up from said bottom section so that said elongated sides can be inserted into said user's respective nostrils, said bight section having bottom and top surfaces, (b) said member having a ribbon configuration, said elongated sides each having two opposing parallel sides that are relatively close together and that join said two opposing edges, said two opposing edges being relatively widely spaced, one of said sides being designated an outwardly facing side and the other being designated an inwardly facing side, said elongated sides each (1) being substantially longer than said bottom section, (2) being generally vertically oriented, and (3) having a free upper end having a widened section or pad, (4) shaped and sized so that when said elongated sides are inserted into the respective nostrils of the user having a nose anatomy within a predetermined range of sizes, said top side of said bottom base section will contact said bottom surface of said user's columella and each of said widened portions or pads at the upper end of each elongated member will engage and urge an outer side of its respective nostril outwardly to dilate said nostril, (c) each elongated side having a bottom section that sandwiches the user's columella when said elongated members are inserted into said user's nostrils and said top surface of said bottom or bight section contacts said user's columella, said bottom section of each elongated side including retention means comprising a protrusion facing the other of the two elongated sides such that, in use, the protrusions overlie said shoulders of said user's columella without exerting a pinching or a horizontal force against said user's septum so as to resist withdrawal of said dilator from said user's nostrils without pinching said user's septum;

wherein said protrusion has a semi-spherical shape.

10. The nasal dilator of claim 9 wherein said member is made of a material selected from the group consisting of plastic, metal, wood, rubber, silicone, hydro-gels, fiber reinforced composites or a combination thereof.

11. The nasal dilator of claim 9 wherein said bottom portion of each elongated side extends up from said bottom base section at a generally right angle and parallel to and spaced from the corresponding portion of the other leg.

12. The nasal dilator of claim 9 wherein a portion of each elongated side above said bottom portion also slopes outwardly, away from the corresponding portion of the other leg, and then extends up vertically to the free upper end.

13. The nasal dilator of claim 9 wherein the semi-spherical shape of each protrusion has a truncated top surface.

14. A nasal dilator configured to be inserted into a user's nostrils for dilating said nostrils to facilitate breathing and increase the volume of airflow, where said user has a nasal septum having a bottom or lower end terminating in a columella having a bottom surface and a pair of shoulders facing upwardly in said user's respective nostrils, comprising:

(a) an elongated U-shaped flexible member having a substantially flat bottom or bight section with a front edge and a back edge and two elongated sides that extend up from said bottom section so that said elongated sides can be inserted into said user's respective nostrils, said bight section having bottom and top surfaces, (b) said member having a ribbon configuration, said elongated sides each having two opposing parallel sides that are relatively close together and that join said two opposing edges, said two opposing edges being relatively widely spaced, one of said sides being designated an outwardly facing side and the other being designated an inwardly facing side, said elongated sides each (1) being substantially longer than said bottom section, (2) being generally vertically oriented, and (3) having a free upper end having a widened section or pad, (4) shaped and sized so that when said elongated sides are inserted into the respective nostrils of the user having a nose anatomy within a predetermined range of sizes, said top side of said bottom base section will contact said bottom surface of said user's columella and each of said widened portions or pads at the upper end of each elongated member will engage and urge the outer side of its respective nostril outwardly to dilate said nostril, (c) each elongated side having a bottom section that sandwiches the user's columella when said elongated members are inserted into said user's nostrils and said top surface of said bottom or bight section contacts said user's columella, said bottom section of each elongated side including retention means comprising a protrusion facing the other of the two elongated sides such that, in use, the protrusions overlie said shoulders of said user's columella without exerting a pinching or horizontal force against said user's septum so as to resist withdrawal of said dilator from said user's nostrils without pinching said user's septum;

wherein said bottom portion of each of said elongated sides has inside and outside surfaces and a pair of edges connecting said inside and outside surfaces so as to define the widths of said inside surfaces, and wherein each protrusion has an elongated shape and the same width as said inside surface of each leg so that each protrusion extends to said pair of edges, each protrusion having top and bottom lateral sides that taper to said inside surface of its respective leg.

15. The nasal dilator of claim 14 wherein each protrusion has a curve or cam shape, and each elongated side having a portion above its protrusion that has the same height as its protrusion so the top surface of the protrusion is defined by an inner surface of the elongated side.

16. A method of adjusting an insertable nose dilator to fit and conform with the shape of a user's nose so that it is comfortable in use yet is able to dilate said user's nostrils, where said dilator comprises an elongated, flexible, elastic member having a generally U-shaped configuration with two upwardly extending sides and a bottom base section, each upwardly extending side having a top section comprising an arm and a bottom section comprising a leg, and a bottom base section connecting said bottom ends of said legs, said bottom base section having a front edge and a back edge, a top side facing upwardly and a bottom side facing downwardly when the sides of said U-shaped member are inserted into the user's respective nostrils, said upwardly extending sides each being (1) substantially longer than said bottom base section, (2) generally vertically oriented, (3) having a free upper end with a widened portion or pad on its outside surface that is initially parallel with the pad of the opposite upwardly extending side, each pad having a front edge and a back edge, and (4) shaped and sized so that when said sides are inserted into the respective nostrils of the user having a nose anatomy within a predetermined range of sizes, and said front edge of said base section is to said user's front side and said back edge of said bottom base section is to said user's back side, said top side of said bottom base section will contact said bottom surf ace of said user's columella and each of said widened portions or pads at the upper end of each arm will engage and urge the outer side of its respective nostril outwardly to dilate said nostril, each of said upwardly extending sides having a protrusion extending toward the other side, said protrusion having an underside spaced from said top side of said bottom base section by a predetermined distance so that when said upwardly extending sides are inserted into the respective nostrils of the user having a nose anatomy within a predetermined range of sizes and said top side of said bottom base section contacts said bottom surface of said user's columella, said underside of said protrusion will overlie an upper side of said user's columella so as to cause said dilator to resist withdrawal from said user's nostrils, and each of said upwardly extending sides and said protrusion being shaped and sized so that they do not exert any pinching or horizontal force against said user's septum, the other leg, or the other protrusion, said method comprising:

(a) comparing said pads of each upwardly extending side with said user's nostrils and, if said user's nostrils are at an angle to each other, bending said front edges of said pads toward each other so that their angle to each other substantially matches the angle of said user's nostrils, (b) comparing a vertical orientation or vertical angle between said pads with the angle between outer sides of said user's nose and bending a top edge of each pad toward a top edge of the other pad so that a vertical angle between said pads matches the angle between said outer sides of said user's nose, (c) comparing a separation between said pads with a separation between the outer edges of said use's nostrils and bending said top sections of said pads outwardly so that said separation between said pads is wider than said separation between outer edges of said use's nostrils, whereby said upwardly extending sides can be bent toward each other so that said pads and said upwardly extending sides can be inserted into said user's nostrils until said bottom base section contacts said user's columella, whereafter said upwardly extending sides can be released to allow said upwardly extending sides to spread apart from each other so that said pads will urge the upper portions of said user's nostrils to spread apart or dilate so that said user will be able to breathe more freely and said dilator will resist withdrawal from said user's nostrils.

* * * * *